United States Patent
Boehringer et al.

(10) Patent No.: US 6,800,650 B2
(45) Date of Patent: Oct. 5, 2004

(54) PYRIDINE AND QUINOLINE DERIVATIVES

(75) Inventors: Markus Boehringer, Moehlin (CH); Bernd Michael Loeffler, Oberrimsingen (DE); Jens-Uwe Peters, Grenzach-Wyhlen (DE); Claus Riemer, Freiburg (DE); Peter Weiss, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/364,490

(22) Filed: Feb. 11, 2003

(65) Prior Publication Data

US 2003/0195188 A1 Oct. 16, 2003

(30) Foreign Application Priority Data

Feb. 13, 2002 (EP) .............................. 02003115

(51) Int. Cl.[7] ...................... A61K 31/47; C07D 215/38; C07D 211/72; C07D 211/84
(52) U.S. Cl. ...................... 514/352; 514/313; 546/162; 546/304; 546/310; 546/312; 546/311
(58) Field of Search ................................ 514/352, 313; 546/162, 304, 310, 312, 311

(56) References Cited

U.S. PATENT DOCUMENTS

| | | |
|---|---|---|
| 6,011,155 A | 1/2000 | Villhauer |
| 6,110,949 A | 8/2000 | Villhauer |
| 6,303,661 B1 | 10/2001 | Demuth et al. |
| 6,319,893 B1 | 11/2001 | Demuth et al. |

FOREIGN PATENT DOCUMENTS

| | | |
|---|---|---|
| DE | 196 16 486 | 10/1997 |
| DE | 198 34 591 | 2/2000 |
| EP | 1 088 818 | 4/2001 |
| WO | WO 98/19998 | 5/1998 |
| WO | WO 99/38501 | 8/1999 |
| WO | WO 00 33839 | 6/2000 |
| WO | WO 00/34241 | 6/2000 |
| WO | WO 01/40180 | 6/2001 |
| WO | WO 01/55105 | 8/2001 |
| WO | WO 01/96295 | 12/2001 |

OTHER PUBLICATIONS

Chorbadjiev, Synthetic COmmunications, vol. 15(5), pp451–457, 1985.*
Bar–Haim, G; Kol, M. Tetrahedron Letters, 1998, vol. 39, pp. 2643–2644.
Chorbadjiev, S., et al., Synthetic Communications, vol. 15(5), pp. 451–457 (1985).

* cited by examiner

*Primary Examiner*—D. Margaret Seaman
(74) *Attorney, Agent, or Firm*—George W. Johnston; Dennis P. Tramaloni; Eileen M. Ebel

(57) ABSTRACT

The present invention provides compounds of formula (I)

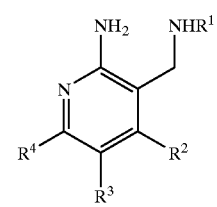

wherein $R^1$, $R^2$, $R^3$ and $R^4$ are as defined in the specification, and pharmaceutically acceptable salts thereof. The compounds are useful for the treatment and/or prophylaxis of diseases which are associated with DPP IV, such as diabetes, particularly non-insulin dependent diabetes mellitus, and impaired glucose tolerance.

17 Claims, No Drawings

PYRIDINE AND QUINOLINE DERIVATIVES

BACKGROUND OF THE INVENTION

The enzyme dipeptidyl peptidase IV (EC.3.4.14.5, abbreviated in the following as DPP-IV) is involved in the regulation of the activities of several hormones. In particular, DPP-IV efficiently and rapidly degrades glucagon-like peptide 1 (GLP-1), which is one of the most potent stimulators of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Vilhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENTION

The present invention provides compounds of the formula (I)

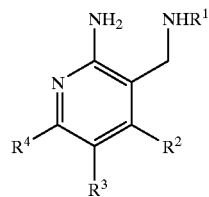

wherein
$R^1$ is hydrogen or lower alkyl;
$R^2$ is heterocyclyl; heterocyclyl mono-, di-, or tri-substituted, independently, by lower alkyl, lower alkoxy, perfluoro-lower alkyl, amino or halogen; aryl; or aryl mono-, di-, or tri-substituted, independently, by halogen, lower alkyl, lower alkoxy, amino or perfluoro-lower alkyl;
$R^3$ and $R^4$ together with the carbon atoms to which they are attached form: a phenyl ring which is optionally mono-, di- or tri-substituted, independently, by halogen, lower alkyl, perfluoro-lower alkyl or lower alkoxy; or
a 5-, 6- or 7-membered saturated ring which optionally contains a heteroatom selected from O, N and S, and which saturated ring is optionally mono-, di- or tri-substituted, independently, by halogen, lower alkyl, perfluoro-lower alkyl or lower alkoxy, said saturated ring being ortho-fused to a 5- or 6-membered aromatic ring which optionally contains a heteroatom selected from O, N and S, and which aromatic ring is optionally mono-, di- or tri-substituted, independently, by halogen, lower alkyl, perfluoro-lower alkyl or lower alkoxy;
and pharmaceutically acceptable salts thereof.

DETAILED DESCRIPTION OF THE INVENTION

We have found novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of Bowl disease, Colitis Ulcerosa, Morbus Crohn, obesity and/or metabolic syndrome. Furthermore, the compounds of the present invention can be used as diuretic agents and for the treatment and/or prophylaxis of hypertension. Unexpectedly, the compounds of the present invention exhibit improved therapeutic and pharmacological properties compared to other DPP IV inhibitors known in the art, such as e.g. in context with pharmacokinetics and bioavailability.

The present invention provides compounds of the formula (I)

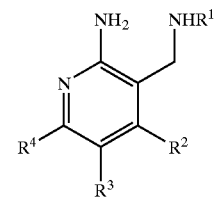

wherein
$R^1$ is hydrogen or lower alkyl;
$R^2$ is heterocyclyl; heterocyclyl mono-, di-, or tri-substituted, independently, by lower alkyl, lower alkoxy, perfluoro-lower alkyl, amino or halogen; aryl; or aryl mono-, di-, or tri-substituted, independently, by halogen, lower alkyl, lower alkoxy, amino or perfluoro-lower alkyl;
$R^3$ and $R^4$ together with the carbon atoms to which they are attached form: a phenyl ring which is optionally mono-, di- or tri-substituted, independently, by halogen, lower alkyl, perfluoro-lower alkyl or lower alkoxy; or
a 5-, 6- or 7-membered saturated ring which optionally contains a heteroatom selected from O, N and S, and which saturated ring is optionally mono-, di- or tri-substituted, independently, by halogen, lower alkyl, perfluoro-lower alkyl or lower alkoxy, said saturated ring being ortho-fused to a 5- or 6-membered aromatic ring which optionally contains a heteroatom selected from O, N and S, and which aromatic ring is optionally mono-, di- or tri-substituted, independently, by halogen, lower alkyl, perfluoro-lower alkyl or lower alkoxy;
and pharmaceutically acceptable salts thereof.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred. Most preferred halogen is chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "perfluoro-lower alkyl" refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred.

The term "alkoxy" refers to the group R'—O—, wherein R' is alkyl. The term "lower-alkoxy" refers to the group R"—O—, wherein R" is lower-alkyl. Examples of lower alkoxy groups are e.g. methoxy, ethoxy, propoxy, isopropoxy, butoxy, isobutoxy and hexyloxy, with methoxy being especially preferred.

The term "heterocyclyl" refers to a saturated, unsaturated or aromatic monovalent cyclic radical containing at least one heteroatom selected from nitrogen, sulfur and oxygen, for example, containing a combination of any of such heteroatoms. Examples of heterocyclyl residues are pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrazinyl, pyrrolidinyl, azepanyl and morpholino. Substituted heterocyclyl residues are heterocyclyl which is mono-, di- or tri-substituted, independently, by halogen, amino, perfluoro-lower alkyl, lower alkyl or lower alkoxy, preferably by lower alkyl or lower alkoxy.

The term "aryl" refers to an aromatic monovalent mono- or polycarbocyclic radical, such as phenyl and naphthyl, preferably phenyl. Substituted aryl is aryl which is mono-, di- or tri-substituted, independently, by lower alkyl, lower alkoxy, halo, amino or perfluoro-lower alkyl, preferably by lower alkyl, lower alkoxy and halogen.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment of the present invention, $R^1$ is lower alkyl, with methyl being preferred. In a preferable embodiment, $R^1$ is hydrogen.

In another embodiment, $R^2$ is heterocyclyl, optionally mono-, di- or tri-substituted, independently, by lower alkyl, lower alkoxy or halogen. Preferred heterocyclyl residues $R^2$ are unsubstituted thienyl and unsubstituted benzo[1,3] dioxolyl.

In a preferable embodiment, $R^2$ is aryl, preferably phenyl, optionally ortho-, meta- or para-, preferably ortho- and para- substituted, independently, by lower alkyl, lower alkoxy, halogen, amino or perfluoro-lower alkyl, preferably by halogen, lower alkyl, perfluoro-lower alkyl or lower alkoxy. Most preferable residue $R^2$ is 2,4-dichloro-phenyl.

In one embodiment, $R^3$ and $R^4$ together with the carbon atoms to which they are attached form a phenyl ring which may optionally be mono-, di- or tri-substituted, independently, by halogen, lower alkyl, perfluoro-lower alkyl or lower alkoxy. Preferably, the said phenyl residue is unsubstituted or mono-substituted by halogen, preferably chlorine, or perfluoro-lower alkyl, preferably trifluoromethyl.

In still another embodiment, $R^3$ and $R^4$ together with the carbon atoms to which they are attached form a 5-, 6- or 7-membered saturated ring (ring A) which may optionally contain a heteroatom selected from O, N and S, and which saturated ring may optionally be mono-, di- or tri- substituted, independently, by halogen, lower alkyl, perfluoro-lower alkyl or lower alkoxy, the said saturated ring being ortho-fused (in relation to the substituted pyridine ring shown in formula I) to a 5- or 6-membered aromatic ring (ring B) which may optionally contain a heteroatom selected from O, N and S, and which aromatic ring may optionally be mono-, di- or tri-substituted, independently, by halogen such as fluorine, chlorine and bromine, lower alkyl such as methyl, perfluoro-lower alkyl such as trifluoromethyl or lower alkoxy such as methoxy.

Above ring A is preferably unsubstituted or substituted by lower alkyl such as methyl. Ring B is preferably phenyl or thienyl, with phenyl being especially preferred, optionally mono-, di- or tri-substituted, independently, by halogen, lower alkyl, perfluoro-lower alkyl or lower alkoxy.

Preferable examples of this embodiment of rings A and B are as follows (showing $R^3$ and $R^4$ together with the carbon atoms to which they are attached and the two double bonds of the pyridine ring shown in formula I extended from said carbon atoms):

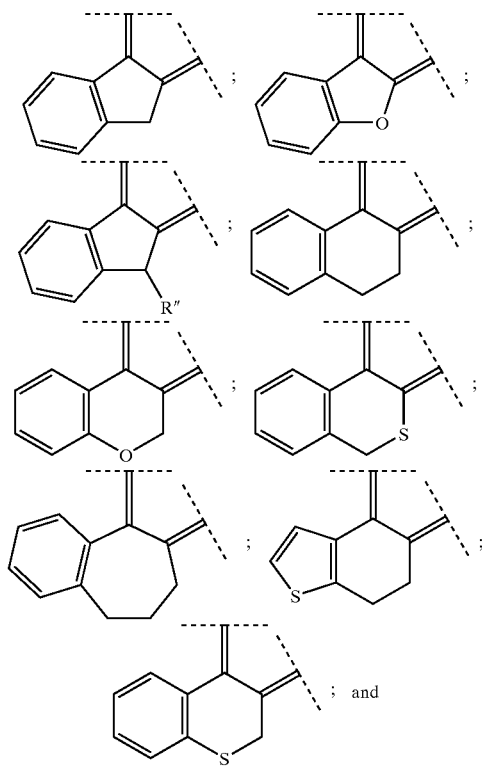

wherein the phenyl moiety can optionally be substituted as defined above and R" is lower alkyl, preferably methyl.

More preferable examples of this embodiment of rings A and B are:

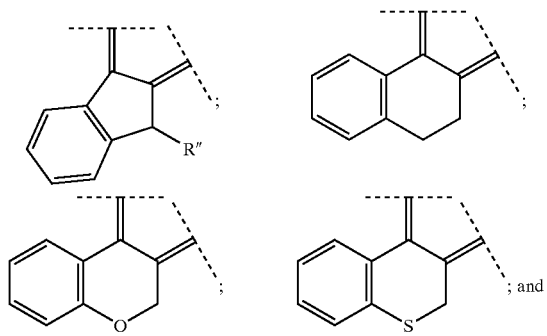

wherein the phenyl moiety can optionally be substituted as defined above and R" is lower alkyl, preferably methyl.

Preferred compounds in accordance with the present invention are those compounds of formula I, wherein $R^1$ is hydrogen;

$R^2$ is phenyl, or phenyl which is ortho-, meta- or para-, preferably ortho- and para-substituted, independently, by lower alkyl such as methyl, halogen such as chlorine and fluorine, lower alkyl such as methyl, perfluoro-lower alkyl such as trifluoromethyl or lower alkoxy such as methoxy, with 2,4-dichloro-phenyl being especially preferred; and $R^3$ and $R^4$ together with the carbon atoms to which they are attached form a 5-, 6- or 7-membered saturated ring which optionally contains a heteroatom selected from O, N and S, and which saturated ring is optionally mono-, di- or tri-substituted, independently, by halogen, lower alkyl, perfluoro-lower alkyl or lower alkoxy, said saturated ring being ortho-fused to a 5- or 6-membered aromatic ring which optionally contains a heteroatom selected from O, N and S, and which aromatic ring is optionally mono-, di- or tri-substituted, independently, by halogen such as fluorine, chlorine and bromine, lower alkyl such as methyl, perfluoro-lower alkyl such as trifluoromethyl, or lower alkoxy such as methoxy.

Preferred compounds of general formula (I) are those selected from the group consisting of:

3-Aminomethyl-4-(2,4-dichloro-phenyl)-5,6-dihydro-benzo[h]quinolin-2-ylamine,

3-Aminomethyl-4-(2,4-dichloro-phenyl)-5H-indeno[1,2-b]pyridin-2-ylamine,

3-Aminomethyl-4-(2,4-dichloro-phenyl)-6,7-dihydro-5H-benzo[6,7]cyclohepta [1,2-b]pyridin-2-ylamine, 3-Aminomethyl-4-(2,4-dichloro-phenyl)-7-methoxy-5H-indeno[1,2-b]pyridin-2-ylamine, 3-Aminomethyl-4-(2,4-dichloro-phenyl)-7,8-dimethoxy-5H-indeno[1,2-b]pyridin-2-ylamine, 3-Aminomethyl-4-(2,4-dichloro-phenyl)-benzo [4,5]furo[3,2-b]pyridin-2-ylamine, 2-Aminomethyl-1-(2,4-dichloro-phenyl)-10H-9-oxa-4-aza-phenanthren-3-ylamine, 3-Aminomethyl-4-(2,4-dichloro-phenyl)-5,6-dihydro-thieno[2,3-h]quinolin-2-ylamine, 2-Aminomethyl-1-(2,4-dichloro-phenyl)-6-fluoro-10H-9-oxa-4-aza-phenanthren-3-ylamine, 2-Aminomethyl-1-(2,4-dichloro-phenyl)-10H-9-thia-4-aza-phenanthren-3-ylamine, 3-Aminomethyl-4-(2,4-dichloro-phenyl)-5-methyl-5H-indeno[1,2-b]pyridin-2-ylamine, 2-Aminomethyl-1-(2,4-dichloro-phenyl)-9H-10-thia-4-aza-phenanthren-3-ylamine, 3-Aminomethyl-4-(2,4-dichloro-phenyl)-10-fluoro-6,7-dihydro-5H-benzo[6,7]cyclohepta[1,2-b]pyridin-2-ylamine, 2-Aminomethyl-1-(2,4-dichloro-phenyl)-10H-9-thia-4-aza-phenanthren-3-ylamine, 3-Aminomethyl-4-(2,4-dichloro-phenyl)-5-methyl-5H-indeno[1,2-b]pyridin-2-ylamine, 2-Aminomethyl-1-(2,4-dichloro-phenyl)-9H-10-thia-4-aza-phenanthren-3-ylamine, 3-Aminomethyl-4-(2,4-dichloro-phenyl)-10-fluoro-6,7-dihydro-5H-benzo[6,7]cyclohepta[1,2-b]pyridin-2-ylamine, 3-Aminomethyl-4-(2,4-dichloro-phenyl)-7-fluoro-5H-indeno[1,2-b]pyridin-2-ylamine, 3-Aminomethyl-4-(2,4-dichloro-phenyl)-8-methyl-5H-indeno[1,2-b]pyridin-2-ylamine, 3-Aminomethyl-4-(2,4-dichloro-phenyl)-9-methoxy-5,6-dihydro-benzo[h]quinolin-2-ylamine, 2-Aminomethyl-6-chloro-1-(2,4-dichloro-phenyl)-10H-9-thia-4-aza-phenanthren-3-ylamine, 3-Aminomethyl-4-(2,4-dichloro-phenyl)-7,9-dimethyl-5,6-dihydro-benzo[h]quinolin-2-ylamine, 2-Aminomethyl-1-(2,4-dichloro-phenyl)-6-methyl-10H-9-oxa-4-aza-phenanthren-3-ylamine, 3-Aminomethyl-7-bromo-4-(2,4-dichloro-phenyl)-5H-indeno[1,2-b]pyridin-2-ylamine, 3-Aminomethyl-4-p-tolyl-quinolin-2-ylamine, 3-Aminomethyl-6-chloro-4-(2-fluoro-phenyl)-quinolin-2-ylamine, 3-Aminomethyl-6-chloro-4-phenyl-quinolin-2-ylamine, 3-Aminomethyl-6-chloro-4-(2-chloro-phenyl)-quinolin-2-ylamine, 3-Aminomethyl-4-phenyl-6-trifluoromethyl-quinolin-2-ylamine, 3-Aminomethyl-4-(2-methoxy-phenyl)-quinolin-2-ylamine, 3-Aminomethyl-4-(2,4-dichloro-phenyl)-quinolin-2-ylamine, 3-Aminomethyl-4-(2-chloro-phenyl)-quinolin-2-ylamine and 3-Aminomethyl-4-(4-chloro-phenyl)-quinolin-2-ylamine, 3-Aminomethyl-4-phenyl-quinolin-2-ylamine, and pharmaceutically acceptable salts thereof.

Compounds of formula I are provided wherein $R^2$ ortho-substituted phenyl can exist in the form of optically pure enantiomers or as racemates. The invention embraces all of these forms.

It will be appreciated, that the compounds of formula (I) in the present invention may be derivatised at functional groups to provide derivatives which are capable of conversion back to the parent compound in vivo.

The compounds of the present invention can be prepared as outlined in Reaction Schemes I and II below:

Reaction Scheme I

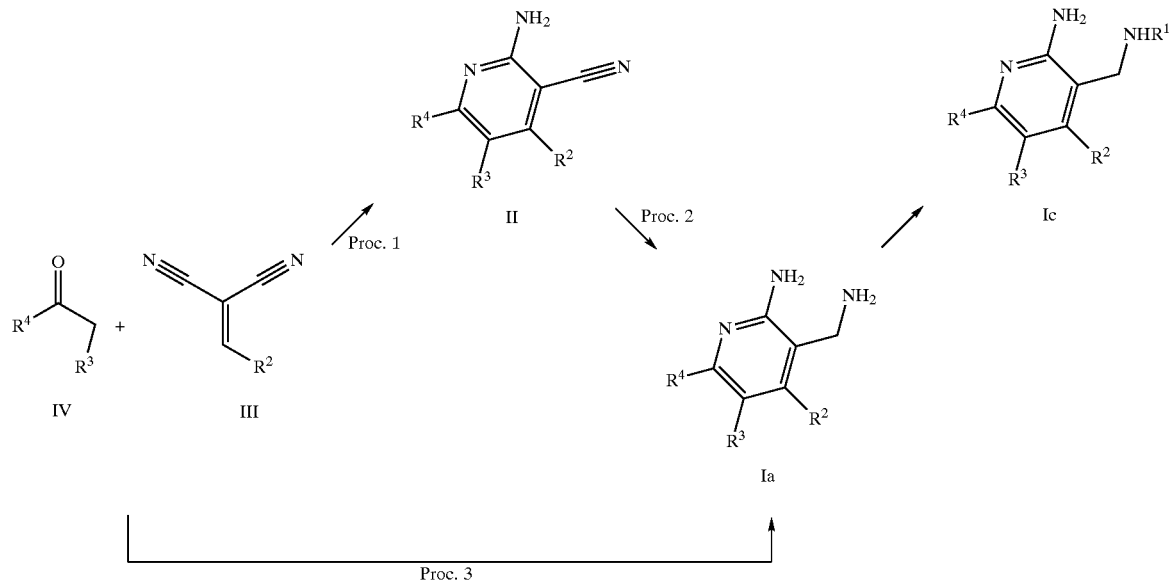

In Reaction Scheme I, $R^3$ and $R^4$ together with the carbon atoms to which they are attached form a 5-, 6- or 7-membered saturated ring which may optionally contain a heteroatom selected from O, N and S, and which saturated ring may optionally be mono-, di- or tri-substituted, independently, by halogen, lower alkyl, perfluoro-lower alkyl or lower alkoxy, the said saturated ring being ortho-fused to a 5- or 6-membered aromatic ring which may optionally contain a heteroatom selected from O, N and S, and which aromatic ring may optionally be mono-, di- or tri-substituted, independently, by halogen, lower alkyl, perfluoro-lower alkyl or lower alkoxy; and $R^2$ and $R^1$ are as defined above.

In Reaction Scheme II, $R^3$ and $R^4$ together with the carbon atoms to which they are attached form a phenyl ring which may optionally be mono-, di- or tri-substituted, independently, by halogen, lower alkyl, perfluoro-lower alkyl or lower alkoxy; and $R^2$ and $R^1$ are as defined above.

The present invention also relates to a process for the manufacture of compounds of formula I. These processes comprise the reduction of nitrites of formula II and VI to amines of formula Ia and Ib, respectively (Procedure 2 in Scheme I and Procedure 5 in Scheme II). This reduction can be performed according to methods known in the art. For example, the reduction can be carried out using a metal hydride such as lithium aluminum hydride in an inert solvent.

Reaction Scheme II

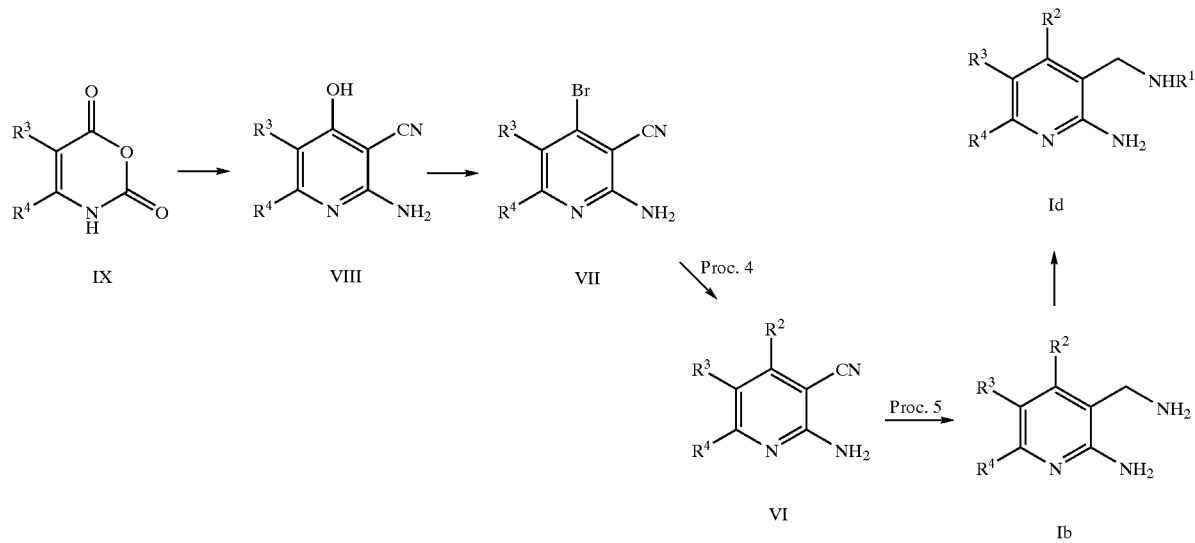

In connection with Procedure 1 of Reaction Scheme I, nitriles of formula II can be prepared by processes known in the art. One such process is the reaction of an arylidene malononitrile III such as 2-(2,4-Dichloro-benzylidene)-malononitrile and a ketone IV such as alpha-Tetralone. For example, the reaction can be performed by heating with ammonium acetate in an inert solvent such as methanol.

In connection with Procedure 4 of Reaction Scheme II, nitriles of formula VI can be prepared from 2-Amino-4-bromo-quinoline-3-carbonitrile and arylboronic acids by a process known in the art as "Suzuki coupling". For example, the reaction can be performed by heating with a palladium compound such as $Pd(OAc)_2$, a base such as $K_3PO_4$, and optionally additives such as phosphino compounds, for instance 2-Dicyclohexyl-phosphino-2'-(N,N-dimethylamino)biphenyl in an inert solvent. 2-Amino-4-bromo-quinoline-3-carbonitrile can be obtained in several steps from isatoic anhydride by processes known in the art.

Further in connection with Reaction Schemes I and II, see Examples 1, 2, 3, 9, 23, 24 and 25. For Procedures 1–5, see Examples 2, 3, 9, 24 and 25, respectively.

Compounds of formulae Ic and Id can be prepared from corresponding compounds of formulae Ia and Ib, respectively, by an alkylation process known in the art (e.g. Bar-Haim, G.; Kol, M. Tetrahedron Lett. 1998, 39, 2663).

The compounds of formula (I) can be manufactured by the methods provided, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier. Pharmaceutically acceptable adjuvants are optionally included.

Further, the invention relates to compounds as defined above for use as therapeutic active substances, particularly as therapeutic active substances for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for use as therapeutic active substances for the treatment and/or prophylaxis of non-insulin dependent diabetes mellitus and/or impaired glucose tolerance. Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP IV such as diabetes, particularly non-insulin dependent diabetes mellitus, impaired glucose tolerance, Bowl disease, Colitis Ulcerosa, Morbus Crohn, obesity, and/or metabolic syndrome, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In context with the methods and uses defined above, the following diseases relate to a preferred embodiment: diabetes, particularly non-insulin dependent diabetes mellitus, impaired glucose tolerance, obesity, and/or metabolic syndrome, preferably non-insulin dependent diabetes mellitus and/or impaired glucose tolerance.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols. Depending on the nature of the active ingredient no carriers might, however, be required in the case of soft gelatine capsules. In such a case, the soft gelatine capsule would be considered a carrier, for the purposes of the present invention. Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile, the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail.

They are, however, not intended to limit its scope in any manner.

EXAMPLES

Abbreviations

NMR=nuclear magnetic resonance spectroscopy, MS=mass spectrometry, aq=aqueous, THF=tetrahydrofuran, DMF=dimethylformamide, DMSO=dimethylsulfoxide, TFA=trifluoroacetic acid, satd.=saturated, r.t.=room temperature, fp.=flash point.

Example 1

Synthesis of Aryl Methylidene Malononitriles 2-(2,4-Dichloro-benzylidene)-malononitrile Under an atmosphere of argon, 2,4-dichlorobenzaldehyde (30.00 g, 171 mmol) and malononitrile (13.59 g, 206 mmol) were suspended in 1-butanol (350 ml). After stirring for 15 min, 8 drops of piperidine were added at room temperature. After stirring for an additional 3 h, diethyl ether was added. The precipitate was filtered and washed with diethyl ether and hexane to give the title compound, MS: m/e=222.8 (M+), as a colorless solid (35.34 g, 92%).

$^1$H-NMR (300 MHz, d$^6$-DMSO, 25° C.): δ(ppm)=7.45 (1H, m), 7.59 (1H, m), 8.18 (2H, m).

Example 2

Synthesis of 2-Amino-nicotinonitriles (Procedure 1 in Reaction Scheme I)

2-Amino-4-(2,4-dichloro-phenyl)-5,6-dihydro-benzo [h]quinoline-3-carbonitrile

A mixture of 2-(2,4-Dichloro-benzylidene)-malononitrile (1.125 g, 5 mmol), alpha-tetralone (735 mg, 5 mmol), ammonium acetate (578 mg, 7.5 mmol), and toluene (5 ml) was stirred for 3 h at reflux. Upon cooling to room temperature, the mixture was taken up in ethyl acetate and extracted with satd. NaHCO$_3$, water, and satd. NaCl, and dried over Na$_2$SO$_4$. The solvent was then evaporated and the title compound (868 mg, 47%), MS: m/e=365.9 (M+H+), was isolated from the residue by column chromatography (silica gel, hexanes, ethyl acetate).

The following 2-amino-nicotinonitriles were prepared in analogy to the procedure described above:

2-Amino-4-(2,4-dichloro-phenyl)-5H-indeno[1,2-b] pyridine-3-carbonitrile, MS: m/e=352.0 (M+H+), was prepared from 1-indanone as a solid (322 mg, 18%).

2-Amino-4-(2,4-dichloro-phenyl)-6,7-dihydro-5H-benzo [6,7]cyclohepta[1,2-b]pyridine-3-carbonitrile, MS: m/e=379.9 (M+), was prepared from 1-benzosuberone as a solid (730 mg, 38%).

2-Amino-4-(2,4-dichloro-phenyl)-7-methoxy-5H-indeno [1,2-b]pyridine-3-carbonitrile, MS: m/e=381.8 (M+), was prepared from 5-methoxy-1-indanone as a solid (715 mg, 37%).

2-Amino-4-(2,4-dichloro-phenyl)-7,8-dimethoxy-5H-indeno[1,2-b]pyridine-3-carbonitrile, MS: m/e=412.0 (M+H+), was prepared from 5,6-dimethoxy-1-indanone as a solid (180 mg, 9%).

2-Amino-4-(2,4-dichloro-phenyl)-benzo[4,5]furo[3,2-b] pyridine-3-carbonitrile, MS: m/e=354.0 (M+H+), was prepared from benzofuran-3(2H)one as a solid (128 mg, 13%).

Example 3

Synthesis of 3-Aminomethyl-pyridin-2-ylamines (Procedure 2 in Reaction Scheme I)

3-Aminomethyl-4-(2,4-dichloro-phenyl)-5,6-dihydro-benzo[h]quinolin-2-ylamine

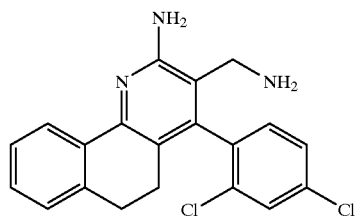

Under an atmosphere of argon, a solution of 2-amino-4-(2,4-dichloro-phenyl)-5,6-dihydro-benzo[h]quinoline-3-carbonitrile (200 mg, 0.58 mmol) in THF (1 ml) is added slowly to a suspension of LiAlH$_4$ (162 mg, 4.26 mmol) in THF (1 ml). After stirring for 2 h at room temperature, the reaction mixture is cooled to −20° C. and water (0.2 ml) is added. After 15 min, ethyl acetate is added and the mixture is filtered through Decalite. The organic phase is then separated, washed with water, and dried over sodium sulfate. Purification by flash chromatography (silica gel, methanol, dichloromethane) affords the title compound, MS: m/e= 369.9 (M+H+), as a light yellow solid (53 mg, 26%).

Example 4

3-Aminomethyl-4-(2,4-dichloro-phenyl)-5H-indeno[1,2-b]pyridin-2-ylamine

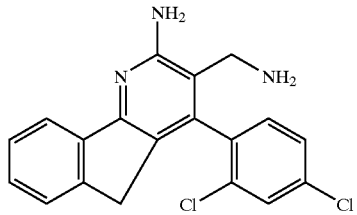

The title compound, MS: m/e=355.8 (M⁺), was prepared from 2-amino-4-(2,4-dichloro-phenyl)-5H-indeno[1,2-b]pyridine-3-carbonitrile in analogy to the process described in Example 3 as a solid (64 mg, 67%).

Example 5

3-Aminomethyl-4-(2,4-dichloro-phenyl)-6,7-dihydro-5H-benzo[6,7]cyclohepta[1,2-b]pyridin-2-ylamine

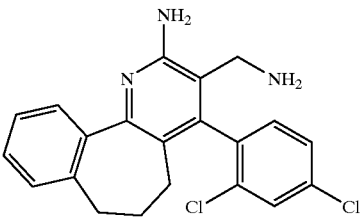

The title compound, MS: m/e=383.9 (M⁺), was prepared from 2-amino-4-(2,4-dichloro-phenyl)-6,7-dihydro-5H-benzo[6,7]cyclohepta[1,2-b]pyridine-3-carbonitrile in analogy to the process described in Example 3 as a solid (40 mg, 25%).

Example 6

3-Aminomethyl-4-(2,4-dichloro-phenyl)-7-methoxy-5H-indeno[1,2-b]pyridin-2-ylamine

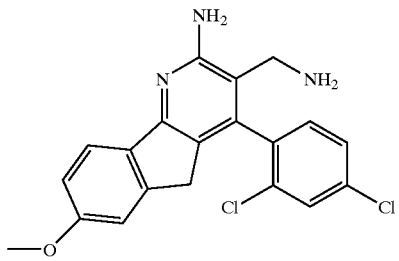

The title compound, MS: m/e=385.9 (M⁺), was prepared from 2-amino-4-(2,4-dichloro-phenyl)-7-methoxy-5H-indeno[1,2-b]pyridine-3-carbonitrile in analogy to the process described in Example 3 as a solid (14 mg, 9%).

Example 7

3-Aminomethyl-4-(2,4-dichloro-phenyl)-7,8-dimethoxy-5H-indeno[1,2-b]pyridin-2-ylamine

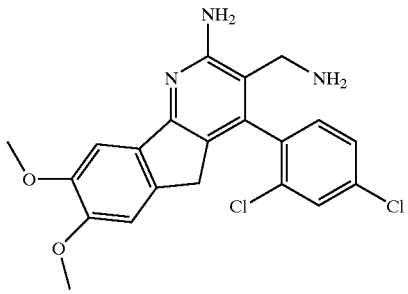

The title compound, MS: m/e 415.9 (M⁺), was prepared from 2-amino-4-(2,4-dichloro-phenyl)-7,8-dimethoxy-5H-indeno[1,2-b]pyridine-3-carbonitrile in analogy to the process described in Example 3 as a solid (9 mg, 6%).

Example 8

3-Aminomethyl-4-(2,4-dichloro-phenyl)-benzo[4,5]furo[3,2-b]pyridin-2-ylamine

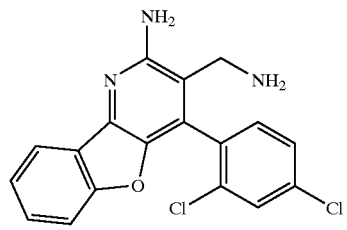

The title compound, MS: m/e=357.8 (M⁺), was prepared from 2-amino-4-(2,4-dichloro-phenyl)-benzo[4,5]furo[3,2-b]pyridine-3-carbonitrile in analogy to the process described in Example 3 as a solid (0.8 mg, 62%).

Example 9

High-throughput synthesis of 3-Aminomethyl-pyridin-2-ylamines from aryl methylidene malononitriles (Procedure 3 in Reaction Scheme I)

2-Aminomethyl-1-(2,4-dichloro-phenyl)-10H-9-oxa-4-aza-phenanthren-3-ylamine

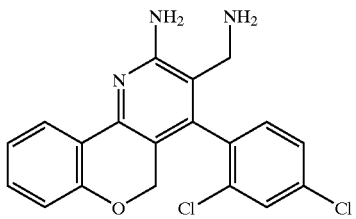

2-(2,4-dichloro-benzylidene)-malononitrile (95 mg, 0.4 mmol), chroman-4-one (59 mg, 0.4 mmol), ammonium acetate (78 mg, 1.2 mmol), and toluene (4 ml) were placed in a reaction vial and shaken overnight at 118° C. Upon cooling and filtration, the solution was evaporated in a vacuum zentrifuge (45° C.) and the residue was purified by automated, preparative HPLC (YMC CombiPrep C18 column 50×20 mm, solvent gradient 5–95% $CH_3CN$ in 0.1% TFA(aq) over 6.0 min, λ=230 nm, flow rate 40 ml/min). The obtained solid (28 mg) was dissolved in THF (1 ml) and added, under an atmosphere of Argon, to a cooled (0° C.) suspension of 100 mg of Lithium aluminum hydride in 1 ml THF in a reaction vial. The reaction mixture was shaken first for 2 h at r.t. and subsequently for 4 h at 40° C. Upon cooling, water was added carefully and the mixture was filtered. The filtrate was evaporated in a vacuum zentrifuge (45° C.). Purification of the re-dissolved (DMF, 1 ml) residue by automated, preparative HPLC (YMC CombiPrep C18 column 50×20 mm, solvent gradient 5–95% $CH_3CN$ in 0.1% TFA(aq) over 6.0 min, λ=230 nm, flow rate 40 ml/min) gave 11 mg (7%) of the title compound, MS: m/e=371.9 (M+H$^+$), as a solid.

Example 10

3-Aminomethyl-4-(2,4-dichloro-phenyl)-5,6-dihydro-thieno[2,3-h]quinolin-2-ylamine

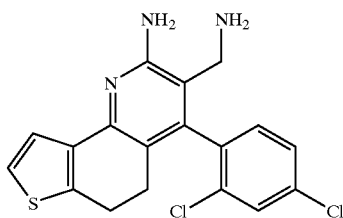

The title compound, MS: m/e=376.0 (M+H$^+$), was prepared from 6,7-Dihydro-5H-benzo[b]thiophen-4-one in analogy to the process described in Example 9 as a solid Example 11

2-Aminomethyl-1-(2,4-dichloro-phenyl)-6-fluoro-10H-9-oxa-4-aza-phenanthren-3-ylamine

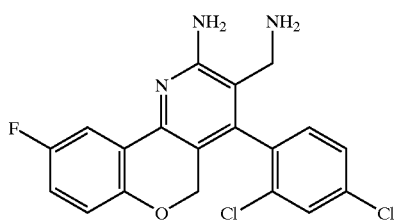

The title compound, MS: m/e=390.2 (M+H$^+$), was prepared from 6-fluoro-chroman-4-one in analogy to the process described in Example 9 as a solid.

Example 12

2-Aminomethyl-1-(2,4-dichloro-phenyl)-10H-9-thia-4-aza-phenanthren-3-ylamine

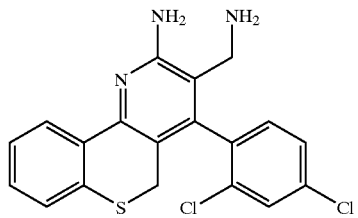

The title compound, MS: m/e=388.2 (M+H$^+$), was prepared from thiochroman-4-one in analogy to the process described in Example 9 as a solid.

Example 13

3-Aminomethyl-4-(2,4-dichloro-phenyl)-5-methyl-5H-indeno[1,2-b]pyridin-2-ylamine

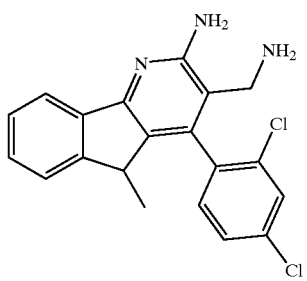

The title compound, MS: m/e=370.1 (M+H$^+$), was prepared from 3-methyl-indan-1-one in analogy to the process described in Example 9 as a solid.

Example 14

2-Aminomethyl-1-(2,4-dichloro-phenyl)-9H-10-thia-4-aza-phenanthren-3-ylamine

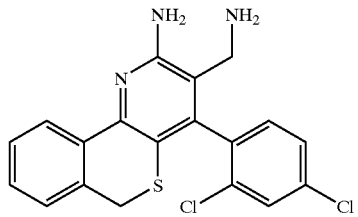

The title compound, MS: m/e=388.2 (M+H$^+$), was prepared from isothiochroman-4-one in analogy to the process described in Example 9 as a solid.

Example 15

3-Aminomethyl-4-(2,4-dichloro-phenyl)-10-fluoro-6,7-dihydro-5H-benzo[6,7]cyclohepta[1,2-b]pyridin-2-ylamine

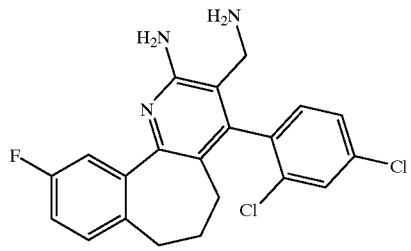

The title compound, MS: m/e=402.0 (M+H⁺), was prepared from 3-fluoro-6,7,8,9-tetrahydro-benzocyclohepten-5-one in analogy to the process described in Example 9 as a solid.

Example 16

3-Aminomethyl-4-(2,4-dichloro-phenyl)-7-fluoro-5H-indeno[1,2-b]pyridin-2-ylamine

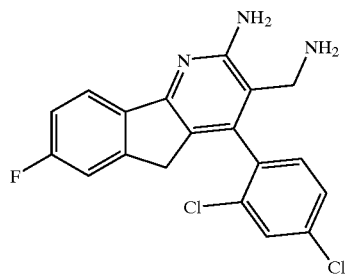

The title compound, MS: m/e 374.3 (M+H⁺), was prepared from 5-fluoro-1-indanone in analogy to the process described in Example 9 as a solid.

Example 17

3-Aminomethyl-4-(2,4-dichloro-phenyl)-8-methyl-5H-indeno[1,2-b]pyridin-2-ylamine

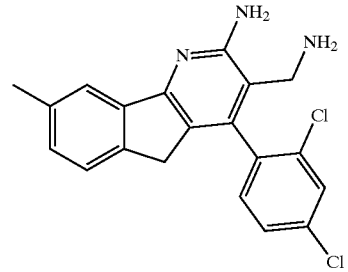

The title compound, MS: m/e=370.0 (M+H⁺), was prepared from 6-methyl-indan-1-one in analogy to the process described in Example 9 as a solid.

Example 18

3-Aminomethyl-4-(2,4-dichloro-phenyl)-9-methoxy-5,6-dihydro-benzo[h]quinolin-2-ylamine

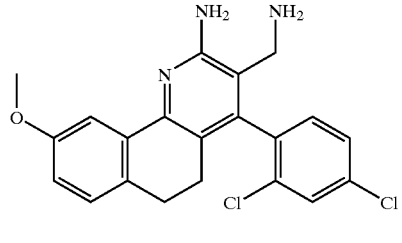

The title compound, MS: m/e=400.3 (M+H⁺), was prepared from 7-methoxy-3,4-dihydro-2H-naphthalen-1-one in analogy to the process described in Example 9 as a solid.

Example 19

2-Aminomethyl-6-chloro-1-(2,4-dichloro-phenyl)-10H-9-thia-4-aza-phenanthren-3-ylamine

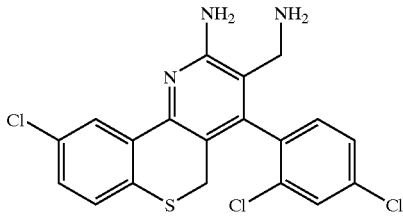

The title compound, MS: m/e=422.0 (M⁺), was prepared from 6-chloro-thiochroman-4-one in analogy to the process described in Example 9 as a solid.

Example 20

3-Aminomethyl-4-(2,4-dichloro-phenyl)-7,9-dimethyl-5,6-dihydro-benzo[h]quinolin-2-ylamine

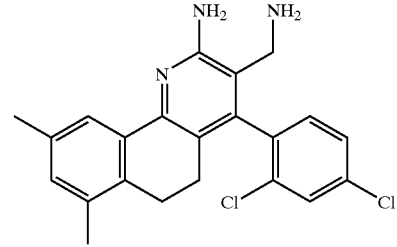

The title compound, MS: m/e=398.0 (M+H⁺), was prepared from 5,7-dimethyl-3,4-dihydro-2H-naphthalen-1-one in analogy to the process described in Example 9 as a solid.

Example 21

2-Aminomethyl-1-(2,4-dichloro-phenyl)-6-methyl-10H-9-oxa-4-aza-phenanthren-3-ylamine

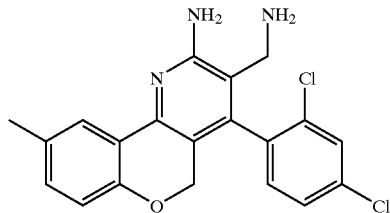

The title compound, MS: m/e=386.2 (M+H$^+$), was prepared from 6-methyl-chroman-4-one in analogy to the process described in Example 9 as a solid.

Example 22

3-Aminomethyl-7-bromo-4-(2,4-dichloro-phenyl)-5H-indeno[1,2-b]pyridin-2-ylamine

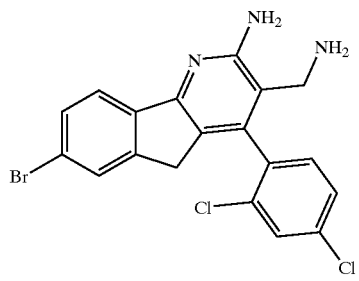

The title compound, MS: m/e=435.0 (M+H$^+$), was prepared from 5-bromo-indan-1-one in analogy to the process described in Example 9 as a solid.

Example 23

Synthesis of quinoline-3-carbonitriles

2-Amino-4-hydroxy-quinoline-3-carbonitrile Sodium hydride (60%, 6.05 g, 151.3 mmol) was added to a solution of Malononitrile (10 g, 151.4 mmol) in DMF (210 ml). After stirring for 30 min at r.t., isatoic anhydride (22.2 g, 136.1 mmol) was added an the mixture was stirred for 30 min at 60° C. The mixture is poured into 1.4 l of ice/water and filtrated. The filtrate was acidified with HCl 37%, stirred for 1 h, and the precipitate isolated. After drying at 40° C. under reduced pressure, the yellow solid was dissolved in DMF (100 ml) and heated to 120° C. for 10 min. After cooling to r.t., the mixture was poured into water (1.5 l), the title compound (24.33 g, 96%), MS: m/e=185.1 (M$^+$), was isolated as a yellow solid by filtration and dried under reduced pressure at 50° C.

2-Amino-4-bromo-quinoline-3-carbonitrile 2-Amino-4-hydroxy-quinoline-3-carbonitrile (6 g, 32.4 mmol) was suspended in acetonitrile (2 l). Phosphorus tribromide (33 g, 11.5 ml, 122 mmol) and bromine (19.15 g, 6.15 ml, 120 mmol) were added and the mixture heated to reflux overnight. The solvent was evaporated under reduced pressure, and the residue was taken up in 1N NaOH. The title compound (5.05 g, 62%), MS: m/e=248.2 (M$^+$), was isolated by filtration, washed with water, and dried.

Example 24

Synthesis of 2-Amino-4-aryl-quinoline-3-carbonitriles (Procedure 4 in Reaction Scheme II)

2-Amino-4-p-tolyl-quinoline-3-carbonitrile 2-Amino-4-bromo-quinoline-3-carbonitrile (248 mg, 1 mmol), 4-Methylphenyl boronic acid (204 mg, 1.5 mmol), Palladium(II)acetate (11 mg, 0.05 mmol), 2-Dicyclohexylphosphino-2'-(N,N-dimethylamino)biphenyl (39 mg, 0.10 mmol), and K$_3$PO$_4$ (425 mg, 2 mmol) were suspended in 4 ml of toluene (Argon atmosphere) and heated to 100° C. for 21 h. The reaction mixture was taken up in diethyl ether, washed with aq. NaOH and brine, and dried over Na$_2$SO$_4$. The solvent was evaporated and the title compound (46 mg, 18%), MS: m/e=259.9 (M$^+$+H), was isolated from the residue by column chromatography (silica gel, Dichloromethane/Methanol=100:0–85:15).

The following 2-Amino-4-aryl-quinoline-3-carbonitriles were prepared in analogy to the procedure described above:

2-Amino-6-chloro-4-(2-fluoro-phenyl)-quinoline-3-carbonitrile, MS: m/e=298.2 (M$^+$+H), was prepared from 2-fluorophenylboronic acid and 2-amino-4-bromo-6-chloro-quinoline-3-carbonitrile as a solid (54 mg, 10%).

2-Amino-6-chloro-4-phenyl-quinoline-3-carbonitrile, MS: m/e=279.8 (M$^+$+H), was prepared from phenylboronic acid and 2-amino-4-bromo-6-chloro-quinoline-3-carbonitrile as a solid (60 mg, 11%).

2-Amino-6-chloro-4-(2-chloro-phenyl)-quinoline-3-carbonitrile, MS: m/e 313.7 (M$^+$+H), was prepared from 2-chlorophenylboronic acid and 2-amino-4-bromo-6-chloro-quinoline-3-carbonitrile as a solid (33 mg, 5%).

2-Amino-4-(2-fluoro-phenyl)-6-phenyl-quinoline-3-carbonitrile, MS: m/e=339.8 (M$^+$+H), was prepared from 2-fluorophenylboronic acid and 2-amino-4-bromo-6-phenyl-quinoline-3-carbonitrile as a solid (72 mg, 12%).

2-Amino-4-phenyl-6-trifluoromethyl-quinoline-3-carbonitrile, MS: m/e=313.8 (M$^+$+H), was prepared from phenylboronic acid and 2-amino-4-bromo-6-trifluoromethyl-quinoline-3-carbonitrile as a solid (47 mg, 6%).

2-Amino-4-(2-methoxy-phenyl)-quinoline-3-carbonitrile, MS: m/e=275.7 (M$^+$+H), was prepared from 2-methoxyphenylboronic acid as a solid (35 mg, 5%).

2-Amino-4-(2,4-dichloro-phenyl)-quinoline-3-carbonitrile, MS: m/e=314.0 (M$^+$+H), was prepared from 2,4-Dichlorophenylboronic acid as a solid (8 mg, 2.4%).

2-Amino-4-(2-chloro-phenyl)-quinoline-3-carbonitrile, MS: m/e=279.9 (M$^+$+H), was prepared from 2-chlorophenylboronic acid as a solid (61 mg, 11%).

2-Amino-4-(4-chloro-phenyl)-quinoline-3-carbonitrile, MS: m/e=279.9 (M$^+$+H), was prepared from 4-chlorophenylboronic acid as a solid (52 mg, 9%).

Example 25

Synthesis of 3-Aminomethyl-4-aryl-quinolin-2-ylamines (Procedure 5 in Reaction Scheme II)

3-Aminomethyl-4-p-tolyl-quinolin-2-ylamine

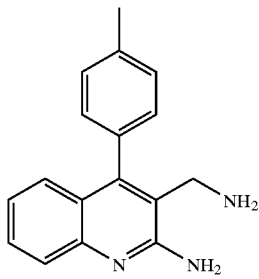

A solution of 2-amino-4-p-tolyl-quinoline-3-carbonitrile (46 mg, 0.177 mmol) in THF (0.5 ml) was added slowly to a suspension of LiAlH$_4$ (67.3 mg, 1.77 mmol) in THF (1 ml) under an atmosphere of argon. The mixture was stirred for 2 h at 40° C. Upon cooling to −20° C., 0.3 ml water added and stirring was continued for 15 min at r.t. The mixture was taken up in ethyl acetate and filtered through dicalite. The filtrate was washed with water and brine, dried (Na$_2$SO$_4$), and evaporated. Purification of the re-dissolved (DMF, 1 ml) residue by automated, preparative HPLC (YMC CombiPrep C18 column 50×20 mm, solvent gradient 5–95% CH$_3$CN in 0.1% TFA(aq) over 6.0 min, λ=230 nm, flow rate 40 ml/min) gave 5 mg (11%) of the title compound as a solid.

Example 26

3-Aminomethyl-6-chloro-4-(2-fluoro-phenyl)-quinolin-2-ylamine

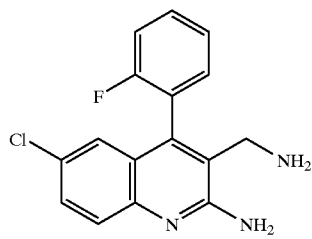

The title compound, MS: m/e=302.0 (M$^+$+H), was prepared from 2-amino-6-chloro-4-(2-fluoro-phenyl)-quinoline-3-carbonitrile in analogy to the process described in Example 25 as a solid (4 mg, 8%).

Example 27

3-Aminomethyl-6-chloro-4-phenyl-quinolin-2-ylamine

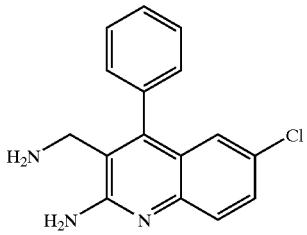

The title compound, MS: m/e=283.1 (M$^+$+H), was prepared from 2-amino-6-chloro-4-phenyl-quinoline-3-carbonitrile in analogy to the process described in Example 25 as a solid (4 mg, 7%).

Example 28

3-Aminomethyl-6-chloro-4-(2-chloro-phenyl)-quinolin-2-ylamine

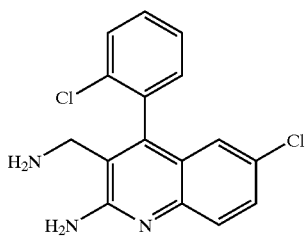

The title compound, MS: m/e=316.9 (M$^+$+H), was prepared from 2-amino-6-chloro-4-(2-chloro-phenyl)-quinoline-3-carbonitrile in analogy to the process described in Example 25 as a solid (3 mg, 10%).

Example 29

3-Aminomethyl-4-phenyl-6-trifluoromethyl-quinolin-2-ylamine

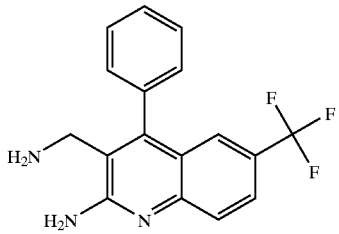

The title compound, MS: m/e=317.3 (M$^+$+H), was prepared from 2-amino-4-phenyl-6-trifluoromethyl-quinoline-3-carbonitrile in analogy to the process described in Example 25 as a solid (4 mg, 9%).

Example 30

3-Aminomethyl-4-(2-methoxy-phenyl)-quinolin-2-ylamine

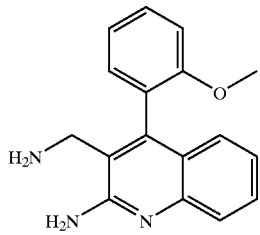

The title compound, MS: m/e=279.1 (M⁺+H), was prepared from 2-amino-4-(2-methoxy-phenyl)-quinoline-3-carbonitrile in analogy to the process described in Example 25 as a solid (1 mg, 2%).

Example 31

3-Aminomethyl-4-(2,4-dichloro-phenyl)-quinolin-2-ylamine

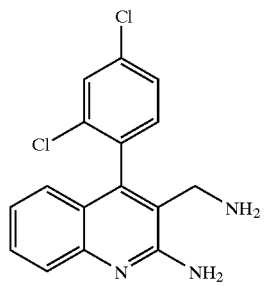

The title compound, MS: m/e=317.1 (M⁺+H), was prepared from 2-amino-4-(2,4-dichloro-phenyl)quinoline-3-carbonitrile in analogy to the process described in Example 25 as a solid (6 mg, 14%).

Example 32

3-Aminomethyl-4-(2-chloro-phenyl)-quinolin-2-ylamine

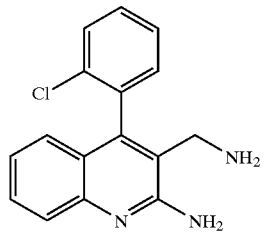

The title compound, MS: m/e=284.0 (M⁺+H), was prepared from 2-amino-4-(2-chloro-phenyl)-quinoline-3-carbonitrile in analogy to the process described in Example 25 as a solid (3 mg, 2%).

Example 33

3-Aminomethyl-4-(4-chloro-phenyl)-quinolin-2-ylamine

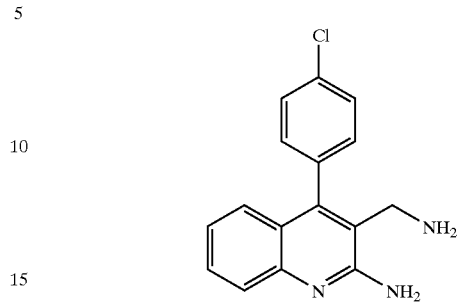

The title compound, MS: m/e=284.0 (M⁺+H), was prepared from 2-amino-4-(4-chloro-phenyl)-quinoline-3-carbonitrile in analogy to the process described in Example 25 as a solid (2 mg, 6%).

Example 34

3-Aminomethyl-4-phenyl-quinolin-2-ylamine

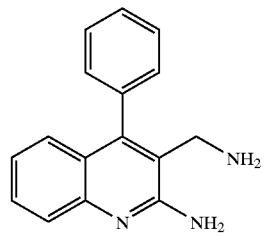

The title compound, fp.: 225–226° C., was prepared from 2-amino-4-phenyl-benzopyridine-3-carbonitrile in analogy to the process described in Example 3 as a light yellow solid (0.56 g, 12%).

Example 35

The following tests were carried out in order to determine the activity of the compounds of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions, and aliquots of 1 ml are shock frozen and stored at −120° C. until used. In the colorimetric DPP-IV assay 5 to 10 µl human plasma, and in the fluorometric assay 1.0 µl of human plasma in a total assay volume of 100 µl is used as an enzyme source. The cDNA of the human DPP-IV sequence of amino acid 31- to 766, restricted for the N-terminus and the transmembrane domain, is cloned into pichia pastoris. The sequence is available under Accession Number NM_001935. It is also disclosed, for example, in Misumi et al. (1992), molecular cloning and sequence analysis of human dipeptidyl peptidase IV, a serine proteinase of the cell surface. Biochim Biophys. Acta 1131(3), 333–336. Human DPP-IV is expressed and purified from the culture medium using conventional column chromatography including size exclusion and anion and cation chromatography. The purity of the final enzyme preparation of Coomassie blue SDS-PAGE is >95%. In the colorimetric DPP-IV assay 20 ng rec.-h DPP-IV and in the fluorometric assay 2 ng rec-h DPP-IV in a total assay volume of 100 μl is used as an enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC50 determinations a final substrate concentration of 50 μM is used. In assays to determine kinetic parameters as Km, Vmax, Ki, the substrate concentration is varied between 10 μM and 500 μM.

In the colorimetric assay H-Ala-Pro-pNA.HCl (Bachem L-1115) is used as a substrate. A 10 mM stock solution in 10% MeOH/H$_2$O is stored at −20° C. until use. In IC50 determinations a final substrate concentration of 200 μM is used. In assays to determine kinetic parameters as Km, Vmax, Ki, the substrate concentration is varied between 100 μM and 2000 μM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA i.e., para-nitroanilin, liberated from the colorimetric substrate is detected in a Packard SpectraCount at 405 nM continuously every 2 minutes for 30 to 120 minutes. Initial rate constants are calculated by best fit linear regression.

DPP-IV activity assays are performed in 96 well plates at 37° C. in a total assay volume of 100 μl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/H$_2$O. The final DMSO concentration in the assay is 1% (v/v). At this concentration enzyme inactivation by DMSO is <5%. Compounds are with (10 minutes at 37° C.) and without preincubation with the enzyme. Enzyme reactions are started with substrate application followed by immediate mixing.

IC50 determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The preferred compounds of the present invention exhibit IC50 values of 1 nM to 10 μM, more preferably of 1–100 nM, as shown in the following table.

| Example | IC50 [μM] |
|---------|-----------|
| 7 | 0.0027 |
| 3 | 0.045 |
| 9 | 0.018 |
| 10 | 0.080 |
| 25 | 1.91 |
| 28 | 1.59 |
| 32 | 0.366 |

Example 36

Galenical Examples

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatine capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatine capsule | |
| Gelatine | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatine capsules of appropriate size. The filled soft gelatine capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesium stearate and the flavouring additives and filled into sachets.

What is claimed is:

1. A compound of formula (I)

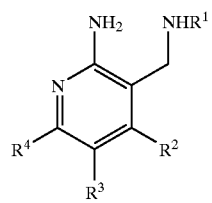

wherein $R^1$ is hydrogen or lower alkyl;

$R^2$ is heterocyclyl; heterocyclyl mono-, di-, or tri-substituted, independently, by lower alkyl, lower alkoxy, perfluoro-lower alkyl, amino or halogen; aryl; or aryl mono-, di-, or tri-substituted, independently, by halogen, lower alkyl, lower alkoxy, amino or perfluoro-lower alkyl;

$R^3$ and $R^4$ together with the carbon atoms to which they are attached form:

a phenyl ring which is optionally mono-, di- or tri-substituted, independently, by halogen, lower alkyl, perfluoro-lower alkyl or lower alkoxy; or a 5-, 6- or 7-membered saturated ring which optionally contains a heteroatom selected from O, N and S, and which saturated ring is optionally mono-, di- or tri-substituted, independently, by halogen, lower alkyl, perfluoro-lower alkyl or lower alkoxy, said saturated ring being ortho-fused to a 5- or 6-membered aromatic ring which optionally contains a heteroatom selected from O, N and S, and which aromatic ring is optionally mono-, di- or tri-substituted, independently, by halogen, lower alkyl, perfluoro-lower alkyl or lower alkoxy;

or a pharmaceutically acceptable salt thereof.

2. The compound according to claim 1, wherein $R^1$ is hydrogen.

3. The compound according to claim 1, wherein $R^2$ is heterocyclyl selected from pyridyl, pyrimidinyl, furyl, thienyl, indolyl, benzo[1,3]dioxolyl, benzofuranyl, benzothiophenyl, dibenzofuranyl, oxazolyl, imidazolyl, thiazolyl, isoxazolyl, pyrazolyl, isothiazolyl, oxadiazolyl, thiadiazolyl, triazolyl, tetrazolyl, oxatriazolyl, thiatriazolyl, pyridazyl, pyrazinyl, pyrrolidinyl, azepanyl and morpholino, which heterocyclyl is optionally mono-, di- or tri-substituted, independently, by halogen, amino, perfluoro-lower alkyl, lower alkyl or lower alkoxy.

4. The compound according to claim 3, wherein $R^2$ is unsubstituted thienyl or unsubstituted benzo[1,3]dioxolyl.

5. The compound according to claim 1, wherein $R^2$ is aryl which is phenyl; or substituted aryl which is phenyl ortho-, meta- or para-substituted, independently, by lower alkyl, lower alkoxy, halogen, amino or perfluoro-lower alkyl.

6. The compound according to claim 5, wherein $R^2$ is 2,4-dichloro-phenyl.

7. The compound according to claim 1, wherein $R^3$ and $R^4$ together with the carbon atoms to which they are attached form a phenyl ring which is optionally mono-, di- or tri-substituted, independently, by halogen, lower alkyl, perfluoro-lower alkyl or lower alkoxy.

8. The compound according to claim 7, wherein $R^3$ and $R^4$ together with the carbon atoms to which they are attached form an unsubstituted phenyl ring or a phenyl ring mono-substituted by halogen or perfluoro-lower alkyl.

9. The compound according to claim 1, wherein $R^3$ and $R^4$ together with the carbon atoms to which they are attached form a 5-, 6- or 7-membered saturated ring which optionally contains a heteroatom selected from O, N and S, and which saturated ring is optionally mono-, di- or tri-substituted, independently, by halogen, lower alkyl, perfluoro-lower alkyl or lower alkoxy, said saturated ring being ortho-fused to a 5- or 6-membered aromatic ring which optionally contains a heteroatom selected from O, N and S, and which aromatic ring is optionally mono-, di- or tri-substituted, independently, by halogen, lower alkyl, perfluoro-lower alkyl or lower alkoxy.

10. The compound according to claim 9, wherein $R^3$ and $R^4$ together with the carbon atoms to which they are attached are selected from the groups

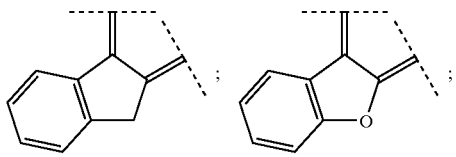

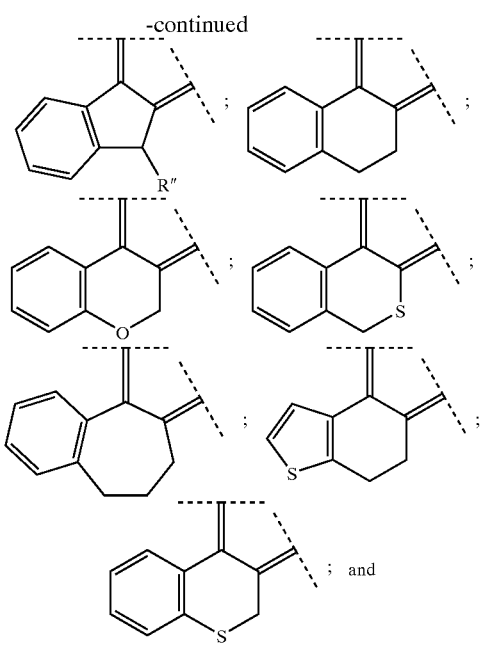

said groups wherein the aromatic ring thereof is mono-, di- or tri-substituted, independently, by halogen, lower alkyl) perfluoro-lower alkyl or lower alkoxy; and R″ is lower alkyl.

11. The compound according to claim 10, wherein $R^3$ and $R^4$ together with the carbon atoms to which they are attached are selected from the groups

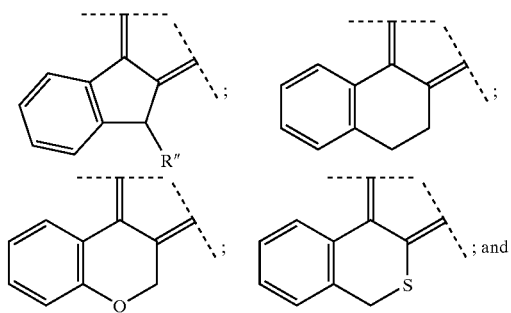

said groups wherein the aromatic ring is mono-, di- or tri-substituted, independently, by halogen, lower alkyl, perfluoro-lower alkyl or lower alkoxy;

and R″ is lower alkyl.

12. The compound according to claim 1, wherein $R^1$ is hydrogen;

$R^2$ is aryl which is phenyl;

or substituted aryl which is ortho-, meta- or para-substituted phenyl, independently, by lower alkyl, halogen, perfluoro-lower alkyl or lower alkoxy;

and $R^3$ and $R^4$ together with the carbon atoms to which they are attached form a 5-, 6- or 7-membered saturated ring which optionally contains a heteroatom selected from O, N and S, and which saturated ring is optionally be mono-, di- or tri-substituted, independently, by halogen, lower alkyl, perfluoro-lower alkyl or lower alkoxy, said saturated ring being ortho-fused to a 5- or 6-membered aromatic ring which contains a heteroatom selected from O, N and S, and which aromatic ring is optionally mono-, di- or tri-substituted, independently, by halogen, lower alkyl, perfluoro-lower alkyl or lower alkoxy.

13. The compound according to claim 1, wherein $R^1$ is hydrogen;

$R^2$ is aryl which is phenyl;

or mono- or di- substituted aryl which is ortho- or para-substituted phenyl, independently, by lower alkyl, halogen, or lower alkoxy;

and $R^3$ and $R^4$ together with the carbon atoms to which they are attached form a phenyl ring which is optionally mono-substituted by halogen or perfluoro-lower alkyl, or $R^3$ and $R^4$ together with the carbon atoms to which they are attached form a 5-, 6- or 7-membered saturated ring which optionally contains a heteroatom selected from O and S, and which saturated ring is optionally mono-substituted by lower alkyl, said saturated ring being ortho-fused to a 5- or 6-membered aromatic ring which optionally contains a sulfur atom in the ring structure, and which aromatic ring is optionally mono- or di-substituted, independently, by halogen, lower alkyl, perfluoro-lower alkyl or lower alkoxy.

14. The compound according to claim 1, selected from the group consisting of:

3-Aminomethyl-4-(2,4-dichloro-phenyl)-5,6-dihydro-benzo[h]quinolin-2-ylamine,

3-Aminomethyl-4-(2,4-dichloro-phenyl)-5H-indeno[1,2-b]pyridin-2-ylamine,

3-Aminomethyl-4-(2,4-dichloro-phenyl)-6,7-dihydro-5H-benzo[6,7]cyclohepta[1,2-b]pyridin-2-ylamine, 3-Aminomethyl-4-(2,4-dichloro-phenyl)-7-methoxy-5H-indeno[1,2-b]pyridin-2-ylamine, 3-Aminomethyl-4-(2,4-dichloro-phenyl)-7,8-dimethoxy-5H-indeno[1,2-b]pyridin-2-ylamine, 3-Aminomethyl-4-(2,4-dichloro-phenyl)-benzo[4,5]furo[3,2-b]pyridin-2-ylamine, 2-Aminomethyl-1-(2,4-dichloro-phenyl)-10H-9-oxa-4-aza-phenanthren-3-ylamine, 3-Aminomethyl-4-(2,4-dichloro-phenyl)-5,6-dihydro-thieno[2,3-h]quinolin-2-ylamine, 2-Aminomethyl-1-(2,4-dichloro-phenyl)-6-fluoro-10H-9-oxa-4-aza-phenanthren-3-ylamine, 2-Aminomethyl-1-(2,4-dichloro-phenyl)-10H-9-thia-4-aza-phenanthren-3-ylamine, 3-Aminomethyl-4-(2,4-dichloro-phenyl)-5-methyl-5H-indeno[1,2-b]pyridin-2-ylamine, 2-Aminomethyl-1-(2,4-dichloro-phenyl)-9H-10-thia-4-aza-phenanthren-3-ylamine, 3-Aminomethyl-4-(2,4-dichloro-phenyl)-10-fluoro-6,7-dihydro-5H-benzo[6,7]cyclohepta[1,2-b]pyridin-2-ylamine, 2-Aminomethyl-1-(2,4-dichloro-phenyl)-10H-9-thia-4-aza-phenanthren-3-ylamine, 3-Aminomethyl-4-(2,4-dichloro-phenyl)-5-methyl-5H-indeno[1,2-b]pyridin-2-ylamine, 2-Aminomethyl-1-(2,4-dichloro-phenyl)-9H-10-thia-4-aza-phenanthren-3-ylamine, 3-Aminomethyl-4-(2,4-dichloro-phenyl)-10-fluoro-6,7-dihydro-5H-benzo[6,7]cyclohepta[1,2-b]pyridin-2-ylamine, 3-Aminomethyl-4-(2,4-dichloro-phenyl)-7-fluoro-5H-indeno[1,2-b]pyridin-2-ylamine, 3-Aminomethyl-4-(2,4-dichloro-phenyl)-8-methyl-5H-indeno[1,2-b]pyridin-2-ylamine, 3-Aminomethyl-4-(2,4-dichloro-phenyl)-9-methoxy-5,6-dihydro-benzo[h]quinolin-2-ylamine, 2-Aminomethyl-6-chloro-1-(2,4-dichloro-phenyl)-10H-9-thia-4-aza-phenanthren-3-ylamine, 3-Aminomethyl-4-(2,4-dichloro-phenyl)-7,9-dimethyl-5,6-dihydro-benzo[h]quinolin-2-ylamine, 2-Aminomethyl-1-(2,4-dichloro-phenyl)-6-methyl-10H-9-oxa-4-aza-phenanthren-3-ylamine, 3-Aminomethyl-7-bromo-4-(2,4-dichloro-phenyl)-5H-indeno[1,2-b]pyridin-2-ylamine, 3-Aminomethyl-4-p-tolyl-quinolin-2-ylamine, 3-Aminomethyl-6-chloro-4-(2-fluoro-phenyl)-quinolin-2-ylamine, 3-Aminomethyl-6-chloro-4-phenyl-quinolin-2-ylamine, 3-Aminomethyl-6-chloro-4-(2-chloro-phenyl)-quinolin-2-ylamine, 3-Aminomethyl-4-phenyl-6-trifluoromethyl-quinolin-2-ylamine, 3-Aminomethyl-4-(2-methoxy-phenyl)-quinolin-2-ylamine, 3-Aminomethyl-4-(2,4-dichloro-phenyl)-quinolin-2-ylamine, 3-Aminomethyl-4-(2-chloro-phenyl)-quinolin-2-ylamine and 3-Aminomethyl-4-(4-chloro-phenyl)-quinolin-2-ylamine, 3-Aminomethyl-4-phenyl-quinolin-2-ylamine, and pharmaceutically acceptable salts thereof.

15. A pharmaceutical composition comprising a compound or a pharmaceutically acceptable salt thereof according to claim 1 and a pharmaceutically acceptable carrier.

16. A method for the treatment or prophylaxis of diabetes or non-insulin dependent diabetes mellitus in a patient in need of such treatment or prophylaxis, which comprises administering a compound or a pharmaceutically acceptable salt thereof according to claim 1 to said patient in an amount of from about 1–1000 mg per day.

17. The method according to claim 16, wherein said amount is from about 1–100 mg per day.

* * * * *